United States Patent [19]

Ford et al.

[11] 4,394,524

[45] Jul. 19, 1983

[54] PREPARATION OF POLYALKYLENE POLYAMINES FROM AMMONIA, ALKYLENEAMINE, AND ALKANOLAMINE

[75] Inventors: Michael E. Ford, Trexlertown; Thomas A. Johnson, Orefield, both of Pa.

[73] Assignee: Air Products and Chemicals, Inc., Allentown, Pa.

[21] Appl. No.: 297,687

[22] Filed: Aug. 31, 1981

[51] Int. Cl.$^3$ ............................................... C07C 85/06
[52] U.S. Cl. ................................. 564/479; 564/480; 564/478; 564/498
[58] Field of Search ..................... 564/479, 480, 478

[56] References Cited

U.S. PATENT DOCUMENTS

| 3,714,259 | 1/1973 | Lichtenwalter et al. | 564/479 |
|---|---|---|---|
| 3,751,474 | 8/1973 | Phillips et al. | 564/479 |
| 3,755,447 | 8/1973 | Klemann et al. | 564/479 |
| 3,869,526 | 3/1975 | Combey et al. | 260/929 |
| 3,869,527 | 3/1975 | Hogberg et al. | 260/946 |
| 4,036,881 | 7/1977 | Brennan et al. | 564/479 |
| 4,044,053 | 8/1977 | Brennan et al. | 564/479 |
| 4,314,083 | 2/1982 | Ford et al. | 564/479 |
| 4,324,917 | 4/1982 | McConnell | 564/479 |

FOREIGN PATENT DOCUMENTS

| 1542359 | 11/1967 | France | 564/479 |
|---|---|---|---|
| 726925 | 3/1955 | United Kingdom | 564/480 |

*Primary Examiner*—John Doll
*Attorney, Agent, or Firm*—Michael Leach; E. Eugene Innis; James C. Simmons

[57] ABSTRACT

A process for preparing noncyclic polyalkylene polyamine compounds is disclosed wherein ammonia, an alkylene polyamine compound and an alkanolamine compound are reacted in the presence of an effective amount of a phosphorus-containing substance or a salt of a sulfur-containing substance or its corresponding acid at a temperature from about 200° to 350° C. under a pressure sufficient to maintain the reaction mixture essentially in liquid phase. The polyalkylene polyamines thus formed are recovered from the reaction mixture.

22 Claims, No Drawings

PREPARATION OF POLYALKYLENE POLYAMINES FROM AMMONIA, ALKYLENEAMINE, AND ALKANOLAMINE

TECHNICAL FIELD

This invention relates to the preparation of polyalkylene polyamines, particularly noncyclic polyalkylene polyamines.

BACKGROUND OF THE INVENTION

One of the early techniques for preparing linear polyalkylene polyamine compounds, such as diethylenetriamine and triethylenetetramine and higher homologs, has been to react an alkyl halide with an amine such as ammonia, ethylenediamine and the like at elevated temperatures and pressures. Generally, high yields of cyclic polyethylene polyamines, e.g., piperazine, aminoethylpiperazine as well as other cyclic amines were produced. Another problem in the process was that hydrohalide salts of ammonia or hydrogen chloride were produced by the reaction, and thus expensive corrosion resistant equipment was required. U.S. Pat. No. 3,751,474 is representative.

More recently, a series of patents disclosed the preparation of linear polyalkylene polyamine compounds by reacting a diol or an alkanolamine compound with an alkylenediamine compound under preselected process conditions. These include:

U.S. Pat. No. 3,714,259 which discloses preparing linear poly(ethylene)amines by contacting ethanolamine with an ethylenediamine compound in the presence of hydrogen and a hydrogenation catalyst. An example of a hydrogenation catalyst is nickel containing copper and chromium components;

U.S. Pat. No. 4,036,881 which discloses the preparation of polyalkylene polyamines by reacting an alkanolamine with an alkyleneamine compound in the presence of a phosphorus-containing substance selected from the group consisting of acidic metal phosphates, phosphoric acid compounds and anhydrides and the phosphate esters; and U.S. Pat. No. 4,044,053 which is somewhat similar to the '881 Patent except that the alkyleneamine compound is present in an excess amount and a diol is used in place of the alkanolamine.

In French Pat. No. 1,542,359 a process is disclosed for the preparation of poly(ethylene)amines by the polymerization of ethanolamine in the presence of carbon dioxide and a strong base such as potassium carbonate or sodium hydroxide.

SUMMARY OF THE INVENTION

It has been found that noncyclic, or linear and branched, polyalkylene polyamines are produced in good yield directly by reacting ammonia, an alkyleneamine compound and an alkanolamine compound in the presence of an effective amount of a phosphorus-containing substance or a salt of a sulfur-containing substance, or the corresponding acid, at a temperature sufficient to effect reaction between the ammonia, alkyleneamine and the alkanolamine under a pressure sufficient to maintain the reaction mixture essentially in liquid phase.

The novel feedstocks for the production of polyalkylene polyamines, comprising mixtures of ammonia, an alkylenediamine and an alkanolamine, afford high selectivity to the commercially valuable noncyclic polyamine products. As another advantage in the production of polyethylene amines, ammonia permits the use of a monoethanolamine:ethylenediamine molar ratio greater than one while still yielding high selectivity to the noncyclic products.

DETAILED DESCRIPTION OF THE INVENTION

The invention relates to a process for synthesizing noncyclic polyalkylene polyamines, and preferably linear and branched polyethylene polyamines such as diethylenetriamine and higher homologs. In the process, an alkyleneamine having two primary amino groups and, preferably, an unbranched alkylene moiety, such as ethylenediamine, is reacted with ammonia and an alkanolamine having a primary or secondary hydroxy moiety and a primary amino group. Preferably, the alkanolamine has an unbranched alkylene moiety.

The alkyleneamine reactants that can be used in practicing the process are represented by the general formula:

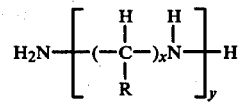

where R is a hydrogen or a lower alkyl ($C_1$-$C_4$) radical, x is a number from 2 to about 6, and y is a number from 1 to about 4. The preferred lower alkyl radical is methyl. Examples of alkyleneamine compounds suited for the reaction include 1,3-propylenediamine, 1,2-propylenediamine, diethylenetriamine, triethylenetetramine and ethylenediamine which is the preferred alkyleneamine compound.

The alkanolamine compounds which are used in practicing the process include those represented by the general formula:

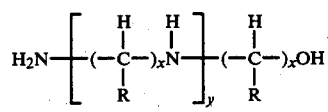

where R is hydrogen to a lower alkyl ($C_1$-$C_4$) radical, x is a number from 2 to about 6, and y is a number from 0 to 3. Methyl is the preferred lower alkyl radical. Examples of alkanolamine compounds that can be used are ethanolamine, isomeric propanolamines, and N-(2-aminoethyl)ethanolamine.

Linear polyalkylene polyamines that are produced by the reaction of ammonia, an alkyleneamine and an alkanolamine are represented by the general formula:

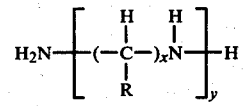

wherein R is hydrogen or a lower alkyl ($C_1$-$C_4$) radical, preferably a methyl radical, x is a number from 2 to about 6, y is a number from 2 to about 7, and x may vary for a given value of y. Examples of linear polyalkylene polyamines that are produced include dipropylenetriamine, tributylenetetramine, di(2-methylethylene)triamine, tri(2-methylethylene)tetramine, N-(2-aminoethyl)-1,3-propylenediamine, diethylenetriamine, triethylenetetramine and tetraethylenepentamine.

The catalysts which are suited for practicing the process described herein are phosphorus-containing substances and salts of a sulfur-containing substance, or the corresponding acid. With respect to the phosphorus-containing substances, such compounds are the phosphorus-containing substances disclosed in U.S. Pat. No. 4,036,881 which is incorporated by reference. This patent teaches that phosphorus-containing substances are useful for the preparation of polyalkylene polyamines by reacting an alkanolamine and an alkyleneamine in their presence.

The present invention is an improvement in which ammonia is also present in the reaction. By adding ammonia, higher selectivity to the commercially desirable noncyclic polyalkylene polyamines is achieved.

Suitable phosphorus-containing substances include, for example, acidic metal phosphates, phosphoric acid compounds and their anhydrides, phosphorous acid compounds and their anhydrides, alkyl or aryl phosphate esters, alkyl or aryl phosphite esters, alkyl or aryl substituted phosphorous acids and phosphoric acids, wherein the alkyl groups have from 1 to about 8 carbon atoms and the aryl groups have from about 6 to about 20 carbon atoms, alkali metal monosalts of phosphoric acid and mixtures of any of the above.

More particularly, suitable acidic metal phosphates include boron phosphate, ferric phosphate, aluminum phosphate, and the like.

Suitable phosphoric acid compounds include aqueous or anhydrous phosphoric acids such as orthophosphoric acid, pyrophosphoric acid, metaphosphoric acid, and condensed phosphoric acids such as polyphosphoric acids. Accordingly, an example of a suitable phosphoric acid is orthophosphoric acid.

In addition, any commercially available mono-, di-, or trialkyl or aryl phosphate or phosphite ester can be employed as the catalyst in the inventive process. Additionally, bis(phosphates) and secondary phosphate esters such as those disclosed in U.S. Pat. Nos. 3,869,526 and 3,689,527, respectively, can be used. Preferably, the lower alkyl esters are employed such as those having from 1 to about 8 carbon atoms per alkyl group. Preferred aryl esters contain from about 6 to about 20 carbon atoms and may include a phenyl group or alkyl-substituted phenyl group.

Further, suitable alkyl or aryl substituted phosphoric acids or phosphorous acids which may be employed as a catalyst include alkyl phosphonic acids, aryl phosphonic acids, alkyl phosphinic acids and aryl phosphinic acids. Preferably, such acids include alkyl or acyl groups and have from 1 to about 8 carbon atoms in each alkyl group and from about 6 to about 20 carbon atoms in each aryl group.

Specific examples of alkyl and aryl substituted phosphorous and phosphoric acids that may be used in accordance with the invention are phenylphosphinic, ethylphosphonic, phenylphosphonic, naphthaphosphonic, and methylphosphinic acids. Examples of the alkyl and aryl substituted phosphorous and phosphoric acid esters are diethyl phenylphosphonate, dimethyl phenylphosphonate, methyl phenylphosphinate, ethyl naphthaphosphinate, and dipropyl methylphosphonate.

It should be noted that the phosphorus-containing substances according to this invention are used in the absence of metal catalysts, such as palladium, platinum, rhodium, ruthenium, nickel or cobalt. In other words, the phosphorus-containing substances according to this invention do not include such metal catalysts bearing phosphorus-containing ligands.

With respect to sulfur-containing substances, the salts are of sulfates and the corresponding acids, typically inorganic sulfates. Virtually any metal salt of the sulfate can be used and these generally include Group I, II, IIIa, IV, IVb–VIIIb metals and include hydrogen, lithium, sodium, potassium, beryllium, magnesium, chromium, manganese, iron, cobalt, zinc, aluminum, antimony, bismuth, tin, ammonium ion and boron. Hydrogen and the ammonium ion are deemed Group I metals for purposes of this invention.

The metal salts of sulfur-containing compounds and their corresponding acids which are suited for practicing the process of this invention are described in more detail in copending application Ser. No. 193,762 filed on Oct. 3, 1980 which issued as U.S. Pat. No. 4,314,083 on Feb. 2, 1982 and is directed to the preparation of polyalkylene polyamines by reacting an alkanolamine and an alkyleneamine in the presence of such sulfur-containing substances, which application is incorporated by reference.

The above mentioned phosphorus- and sulfur-containing substances are not intended to be exhaustive of those which may be employed as a catalyst material in the process of the present invention. Those materials are set forth to specify types of phosphorus- and sulfur-containing compounds that a worker in the art may use as a catalyst material. However, as might be expected, it is preferred to use those which are more reactive and provide for substantial conversion with high selectivity to the noncyclic polyalkyleneamine product. The preferred catalyst compounds include beryllium sulfate, boron sulfate, ammonium sulfate, and boron phosphate.

The quantity of phosphorus-containing or sulfur-containing substance used in the reaction is somewhat empirical and can vary widely depending upon the reactivity of the catalyst and the reactivity of the reactants present. An effective amount of material is used; in other words, an amount which causes a reaction involving ammonia, the alkyleneamine and the alkanolamine to yield noncyclic polyalkylene polyamine products at the temperature and pressure used. Usually, though, the amount used to provide a catalytic effect ranges from about 0.1 to 25 mole % based upon the total amount of the alkyleneamine and alkanolamine feed present in the reaction mixture, and preferably is an amount of about 0.1 to 10.0 mole %. Within these ranges though, the level of catalyst again is somewhat empirical and is adjusted depending on the product state desired. Generally, as the level of the catalyst increases and conversion increases, selectivity is somewhat reduced. Therefore, in those instances where there is substantial catalytic activity, the quantity of catalyst may be reduced to increase selectivity with a concomitant reduction in conversion.

In the preparation of noncyclic polyalkylene polyamines, and preferably the noncyclic polyethylene polyamines, the reaction is maintained at a temperature of from about 200° C. to about 350° C., and preferably from about 275° C. to 325° C. The pressure utilized for carrying out the reaction is that autogenous pressure which is sufficient to maintain the reaction essentially in liquid phase although higher pressures can be used. When utilizing these temperatures and pressures, the reaction is allowed to proceed until a desired conversion is obtained or the reaction is complete. Normally, the reaction is carried out within about 0.5 to 3.0 hours.

Generally, the mole ratio of alkyleneamine compound to alkanolamine compound may range from about 10:1 to 1:10, and preferably is about 5:1 to 1:5. It is advantageous in carrying out the process that the proportion of alkyleneamine compound to alkanolamine compound be in stoichiometric excess, e.g., from about 1:1 up to 5:1, to result in highest selectivity to noncyclic product. When the alkyleneamine compound approaches a 1:1 molar ratio with the alkanolamine, or falls below that level, the alkanolamine may have a tendency to form the cyclic amine compositions although the addition of ammonia as a reactant greatly diminishes this tendency. Accordingly, the most preferred molar ratio range of alkyleneamine compound to alkanolamine compound is from about 1:1 to 3:1.

With respect to the amount of ammonia present in the reaction mixture, the molar quantity of ammonia may range from about 0.5:1.0 to 10:1.0 with respect to the alkyleneamine compound and the alkanolamine compound and preferably is about 2:1 to 10:1 although large excess quantities of ammonia can be used.

It is preferred when reacting ethylenediamine (EDA) and monoethanolamine (MEA) with ammonia that the mole ratios be in the range of 1-2:1-2:1-10 (EDA:MEA:$NH_3$).

Recovery of the noncyclic polyalkylene polyamines from the reaction mixture can be accomplished by conventional techniques, these techniques generally involving a distillation. Often a small amount of a salt, such as the one used as the catalytic material, is added to the polyalkylene polyamine separation purification as described in U.S. Pat. No. 3,755,447.

Without wishing to be bound by any particular theory, it appears that the enhancement in alkyleneamine/alkanolamine copolymerization by the inclusion of ammonia in the reactant mixture can be explained by the following using ethylenediamine and monoethanolamine as the representative reactants:

In the presence of appropriate catalysts the hydroxy group of monoethanolamine reacts with the amino group of ethylenediamine to form polyamines and water. However, in addition to containing a hydroxy group, monoethanolamine also has an amino group. In the presence of ethylenediamine and polyamine-forming catalysts, monoethanolamine not only can react with the amino group of ethylenediamine to form polyamines, but it also can react with the amino group of another monoethanolamine molecule. The product of this reaction is hydroxyethylethylenediamine. However, hydroxyethylethylenediamine still contains both an amino group and a hydroxy group. Not only can these groups react to form a cyclic amine, but they are also very favorably situated by the geometry of the hydroxyethylethylenediamine molecule for cyclization to produce the six-membered heterocyclic polyamine, piperazine. In fact, the very favorable orientation of the hydroxy and amino groups of hydroxyethylethylenediamine and the very favorable thermodynamics of the cyclization to form piperazine essentially preclude reaction of hydroxyethylethylenediamine with an alkyleneamine to form a noncyclic polyamine. Self-condensation of monoethanolamine to form hydroxyethylethylenediamine and facile intramolecular cyclization of hydroxyethylethylenediamine to form piperazine constitute the source of cyclic polyamines in copolymerizations of ethylenediamine and monoethanolamine. Higher cyclic polyamines are derived from piperazine by the continued reaction with monoethanolamine.

The initial step by which cyclic polyamines are formed, the self-condensation of monoethanolamine, operates whenever significant amounts of monoethanolamine are included in a copolymerization of monoethanolamine and ethylenediamine. Obviously, this self-condensation is most prevalent when monoethanolamine is the major reactant in the polyamine-forming reaction, that is to say, when the monoethanolamine:ethylenediamine mole ratio is greater than 1. However, even when monoethanolamine is the lesser, but still a significant reactant in the polyamine-forming reaction, i.e., monoethanolamine:ethylenediamine mole ratio less than 1, the sequence of monoethanolamine self-condensation and hydroxyethylethylenediamine cyclization can still occur.

We believe that the inclusion of ammonia in the reaction of monoethanolamine and ethylenediamine reduces the amount of self-condensation of monoethanolamine, and consequently, also reduces the amount of cyclic polyamines that are formed. When ammonia is added to the reaction mixture of monoethanolamine and ethylenediamine, the monoethanolamine can react not only with ethylenediamine to form polyamines, and with itself to form cyclic polyamines, but also with ammonia to form ethylenediamine. By this route, more ethylenediamine is available for reaction with the remaining monoethanolamine. Thus, not only does monoethanolamine have another amine (ammonia) with which to react, but ethylenediamine formed by reaction of monoethanolamine with ammonia continues to react with additional monoethanolamine to form higher noncyclic polyamines.

The overall effect of inclusion of ammonia is to divert monoethanolamine away from its self-condensation reaction, which forms cyclic polyamines, to the production of ethylenediamine and higher noncyclic polyamines. Needless to say, the degree of this effect is most pronounced at high monoethanolamine levels. However, even at relatively low monoethanolamine levels operation of this effect diverts a significant amount of monoethanolamine away from the formation of cyclic polyamines to the production of the desired noncyclic polyamines.

The following examples which illustrate the nature of the process described herein are not intended to limit the scope of the invention. In each example the reaction was carried out under that autogenous pressure which was sufficient to maintain the reaction in essentially liquid phase at the reaction temperature. Analysis of the cooled samples of each example was by gas-liquid chromatography.

Although examples of batch processes are presented, such examples are not intended to preclude the practice of the process of this invention in a continuous process.

EXAMPLE 1

A mixture of ethylenediamine (40 gm., 0.67 mole), monoethanolamine (20 gm., 0.33 mole), ammonia (32 gm., 1.88 mole), and beryllium sulfate (9.1 gm., 0.05 mole) was placed in a 300 ml stainless steel autoclave. The mole ratio of ethylenediamine:monoethanolamine:ammonia (EDA:MEA:$NH_3$) was 2:1:5.7; the level of catalyst incorporation was 5 mole %, based on ethylenediamine and monoethanolamine. The mixture was heated to 300° C. and stirred at 2,000 rpm.

Samples of the reaction mixture were withdrawn after 0.5 and 1.0 hours at 300° C.

EXAMPLE 2

A mixture of ethylenediamine (22.5 gm., 0.375 mole), monoethanolamine (40 gm., 0.66 mole), ammonia (32 gm., 1.88 mole), and beryllium sulfate (9.1 gm., 0.05 mole) was placed in a 300 ml stainless steel autoclave. The mole ratio of EDA:MEA:NH$_3$ was 1:1.76:5.0; the level of catalyst incorporation was 4.8 mole %, based on ethylenediamine and monoethanolamine. The mixture was heated to 300° C. for 2 hours and stirred at 2,000 rpm.

EXAMPLE 3

The procedure of Example 2 was repeated using 40 gm. (0.67 mole) ethylenediamine, 20 gm. (0.33 mole) monoethanolamine, 32 gm. (1.88 mole) ammonia and 2.48 gm. (0.008 mole) boron sulfate which corresponds to a EDA:MEA:NH$_3$ mole ratio of 2:1:5.7 and a level of catalyst incorporation of 0.8 mole %, based on ethylenediamine and monoethanolamine.

EXAMPLE 4

The procedure of Example 2 was repeated using 22.5 gm. (0.375 mole) ethylenediamine, 40 gm. (0.66 mole) monoethanolamine, 32 gm. (1.88 mole) ammonia and 2.48 gm. (0.008 mole) boron sulfate which corresponds to a EDA:MEA:NH$_3$ mole ratio of 1:1.76:5.0 and a level of catalyst incorporation of 0.77 mole %, based on ethylenediamine and monoethanolamine.

EXAMPLE 5

The procedure of Example 2 was repeated using 40 gm. (0.67 mole) ethylenediamine, 20 gm. (0.33 mole) monoethanolamine, 32 gm. (1.88 mole) ammonia and 6.6 gm. (0.05 mole) ammonium sulfate which corresponds to a EDA:MEA:NH$_3$ mole ratio of 2:1:5.7 and a level of catalyst incorporation of 5.0 mole %, based on ethylenediamine and monoethanolamine.

EXAMPLE 6

The procedure of Example 5 was repeated excluding ammonia. Upon cooling the reaction mixture was found to consist of a darkly colored solid mass. The product was soluble in aqueous 1.0 M hydrochloric acid, an indication of the presence of amine functionality. However, attempted gas liquid chromatographic analysis of the product revealed that no volatile polyamines, i.e., polyamines with molecular weights less than or equal to the isomeric tetraethylenepentamines, had been formed. Thus, all of the ethylenediamine and monoethanolamine feedstock had been converted to solid, high molecular weight polyamines, and none had been converted to the desired volatile noncyclic polyamines.

EXAMPLE 7

The procedure of Example 6 which contained no ammonia was repeated using 2.31 gm. (0.0175 mole) ammonium sulfate. The mole ratio of ethylenediamine:monoethanolamine was 2:1 and the level of catalyst incorporation was 1.75 mole %, based on ethylenediamine and monoethanolamine. Analysis indicated a substantial conversion to a mixture of polyamines; however, the mixture consisted of substantial amounts of cyclic polyamines.

EXAMPLE 8

The procedure of Example 2 was repeated using 20 gm. (0.33 mole) ethylenediamine, 40 gm. (0.66 mole) monoethanolamine, 56.5 gm. (3.32 mole) ammonia and 5.3 gm. (0.05 mole) boron phosphate which corresponded to a EDA:MEA:NH$_3$ mole ratio of 1:2:10 and a level of catalyst incorporation of 5 mole %, based on ethylenediamine and monoethanolamine.

EXAMPLE 9

This run, which attempted to duplicate the art for comparative purposes in terms of the composition of the feedstock for producing polyalkylene polyamines as taught by U.S. Pat. No. 4,036,881, was performed according to the procedure of Example 8 of this disclosure omitting ammonia from the reaction mixture. Analysis of the cooled reaction mixture by gas-liquid chromatography indicated substantial conversion to a mixture of polyamines. However, the product consisted primarily of the less desirable cyclic polyamines.

EXAMPLE 10

The procedure of Example 9 was repeated again excluding ammonia. However, the mole ratio of ethylenediamine:monoethanolamine was 2:1 and the level of catalyst was 5 mole %, based on ethylenediamine and monoethanolamine. Analysis of the cooled reaction mixture by gas liquid chromatography indicated substantial conversion to a mixture of polyamines; however, the mixture did not consist of predominantly noncyclic polyamines.

EXAMPLE 11

The procedure of Example 2 was repeated using 60 gm. (1.0 mole) ethylenediamine, 30 gm. (0.49 mole) monoethanolamine, 42.5 gm. (2.5 mole) ammonia and 8 gm. (0.075 mole) boron phosphate which corresponds to a EDA:MEA:NH$_3$ mole ratio of 2:1:5 and a 5 mole % level of catalyst incorporation based on ethylenediamine and monoethanolamine.

EXAMPLE 12

The procedure of Example 2 was repeated using 30 gm. (0.5 mole) ethylenediamine, 15 gm. (0.24 mole) monoethanolamine, 42.1 gm. (2.48 mole) ammonia and 4 gm. (0.038 mole) boron phosphate which corresponded to a EDA:MEA:NH$_3$ mole ratio of 2:1:10 and a 5 mole % level of catalyst incorporation based on ethylenediamine and monoethanolamine.

TABLE 1

POLYETHYLENE AMINES FROM ETHYLENEDIAMINE, MONOETHANOLAMINE, AND AMMONIA

| EXAMPLE | CATALYST LEVEL (MOLE %) | EDA | PIP | AEP | DETA | TETA (NC) | TETA (C) | TEPA (NC) | TEPA (C) | NC$^a$ |
|---|---|---|---|---|---|---|---|---|---|---|
| 1A (0.5 hr) | 5.0 | b | 2.45 | 0.66 | 50.13 | 7.55 | 2.36 | 0.0 | 0.0 | 91 |
| 1B (1.0 hr) | 5.0 | b | 2.92 | 2.27 | 39.08 | 7.25 | 1.76 | 0.0 | 0.0 | 87 |
| 2 | 4.8 | b | 4.74 | 4.66 | 12.18 | 3.93 | 3.16 | 0.48 | 0.28 | 56 |
| 3 | 0.8 | b | 2.39 | 2.69 | 14.14 | 1.43 | 3.84 | 0.0 | 0.0 | 63 |

TABLE 1-continued
POLYETHYLENE AMINES FROM ETHYLENEDIAMINE, MONOETHANOLAMINE, AND AMMONIA

| EXAMPLE | | CATALYST LEVEL (MOLE %) | EDA | PIP | AEP | DETA | TETA (NC) | TETA (C) | TEPA (NC) | TEPA (C) | NC[a] |
|---|---|---|---|---|---|---|---|---|---|---|---|
| 4 | | 0.77 | b | 6.16 | 2.46 | 13.98 | 4.12 | 4.20 | 0.0 | 0.0 | 58 |
| 5 | | 5.0 | b | 0.91 | 0.96 | 14.60 | 0.84 | 3.52 | 0.0 | 0.0 | 74 |
| 6 | (no NH$_3$) | 5.0 | b | 0.0 | 0.0 | 0.0 | 0.0 | 0.0 | 0.0 | 0.0 | 0 |
| 7 | (no NH$_3$) | 1.75 | b | 5.97 | 1.68 | 9.79 | 0.0 | 2.19 | 0.0 | 0.0 | 50 |
| 8 | | 5.0 | b | 3.16 | 2.85 | 21.32 | 6.66 | 2.28 | 1.73 | 0.0 | 78 |
| 9 | (no NH$_3$) | 5.0 | b | 3.46 | 8.04 | 3.27 | 1.04 | 8.71 | 0.31 | 17.11 | 11 |
| 10 | (no NH$_3$) | 5.0 | b | 9.97 | 12.84 | 15.41 | 6.80 | 8.46 | 4.38 | 4.98 | 42 |
| 11 | | 5.0 | b | 1.52 | 2.17 | 24.41 | 5.98 | 1.38 | 2.33 | 0.28 | 86 |
| 12 | | 5.0 | b | 3.14 | 0.81 | 24.05 | 6.08 | 2.40 | 1.44 | 0.96 | 81 |

Weight percent of components in product mixture on a feedstock-free basis
EDA = Ethylenediamine
PIP = Piperazine
AEP = N-(2-aminoethyl)piperazine
DETA = Diethylenetriamine
TETA (NC) = Triethylenetriamine (noncyclic isomers)
TETA (C) = Triethylenetriamine (cyclic isomers)
TEPA (NC) = Tetraethylenepentamine (noncyclic isomers)
TEPA (C) = Tetraethylenepentamine (cyclic isomers)
[a]Weight percent of noncyclic products
[b]Feedstock

TABLE 2

| EXAMPLE | CATALYST (level)[a] | FEED RATIO[b] | SELECTIVITY (NC %)[c] | CONVERSION (%)[d] | YIELD (%)[e] |
|---|---|---|---|---|---|
| 1A (0.5 hr) | Beryllium Sulfate (5.0) | 2/1/5.7 | 91 | 15.4 | 14.0 |
| 1B (1.0 hr) | Beryllium Sulfate (5.0) | 2/1/5.7 | 87 | 25.9 | 22.5 |
| 2 | Beryllium Sulfate (5.0) | 1/1.76/5.0 | 56 | 39.9 | 22.3 |
| 3 | Boron Sulfate (0.8) | 2/1/5.7 | 63 | 51.0 | 32.1 |
| 4 | Boron Sulfate (0.8) | 1/1.76/5.0 | 58 | 26.0 | 15.1 |
| 5 | Ammonium Sulfate (5.0) | 2/1/5.7 | 74 | 42.9 | 31.7 |
| 6 (no NH$_3$) | Ammonium Sulfate (5.0) | 2/1/0 | 0 | 100 | — |
| 7 (no NH$_3$) | Ammonium Sulfate (1.75) | 2/1/0 | 50 | 21.4 | 10.7 |
| 8 | Boron Phosphate (5.0) | 1/2/10 | 78 | 61.7 | 48.1 |
| 9 (no NH$_3$) | Boron Phosphate (5.0) | 1/2/0 | 11 | 84.6 | 9.3 |
| 10 (no NH$_3$) | Boron Phosphate (5.0) | 2/1/0 | 42 | 66.2 | 27.8 |
| 11 | Boron Phosphate (5.0) | 2/1/5 | 86 | 57.0 | 49.0 |
| 12 | Boron Phosphate (5.0) | 2/1/10 | 81 | 53.3 | 43.2 |

[a]Mole percent catalyst, based on ethylenediamine and monoethanolamine
[b]Mole ratio ethylenediamine:monoethanolamine:ammonia
[c]Noncyclic components in products mixture
[d]Based on ethylenediamine and monoethanolamine
[e]Yield (polyethylene amines) = selectivity × conversion/100

Table 1 shows the data of Examples 1 to 12 in terms of the weight percent of the various individual polyamines in the product mixture on a feedstock-free basis. As can be seen from the data in Table 1, all the Examples which included ammonia in the reactant mixture comprising ethylenediamine and monoethanolamine showed good conversion to a mixture of predominantly noncyclic polyamines. In particular, superior yields of the desirable linear product diethylenetriamine [DETA] were achieved in the ammonia-containing runs in contrast to the corresponding Examples which contained the same catalyst but no ammonia. See Examples 5, 6 and 7 with respect to ammonium sulfate and Examples 8 and 9, and 10, 11 and 12 with respect to boron phosphate.

Using boron phosphate as a catalyst without the addition of ammonia (Examples 9 and 10) as taught in the prior art, produced much higher amounts of cyclic polyethylene amines than the corresponding boron phosphate and ammonia-containing Examples having the same ethylenediamine:monoethanolamine molar ratio. The production of cyclic triethylenetetramines [TETA(C)] was more than twice that in any of the ammonia-containing runs. With respect to the production of cyclic tetraethylenepentamines [TEPA(C)] the yield of these isomers in Examples 9 and 10 was about 17 wt % and 5 wt %, respectively, while the corresponding ammonia-containing runs produced less than 1 wt % of cyclic tetraethylenepentamines.

Examples 8 and 9 were duplicate runs in which ammonia was present in the reactant feed stream of Example 8 and was absent in the feed stream of Example 9. The mole ratio of ethylenediamine:monoethanolamine was 1:2 and the catalyst level was 5% in each case. A comparison of the product data shows that in Example 8 the noncyclic products diethylenetriamine [DETA], triethylenetetramine [TETA(NC)] and tetraethylenepentamine [TEPA(NC)] were produced in much greater amounts. Example 9 produced significantly greater quantities of the cyclic products N-(2-aminoethyl)piperazine [AEP], triethylenetetramine [TETA(C)] and tetraethylpentamine [TEPA(C)].

Similarly, Examples 10, 11 and 12 were duplicate runs in which ammonia was present in the reactant feed stream of Examples 11 and 12 and was excluded in Example 10. The mole ratio of ethylenediamine:monoethanolamine was 2:1 and the catalyst level was 5% in each run. Again the ammonia-containing runs of Examples 11 and 12 demonstrated superior production of diethylenetriamine [DETA] and superior selectivity in terms of the percent of noncyclics in the products mixture. Interestingly, Example 10 gave higher yields of the noncylic triethylenetetramine [TETA (NC)] and tetraethylenepentamine [TEPA (NC)]. However, Example 10 also resulted in much greater amounts of all the cyclic amines.

The ammonium sulfate catalyzed runs used an ethylenediamine:monoethanolamine molar ratio of 2:1, but Example 5 which included ammonia produced greater relative quantities of noncyclic products.

Therefore, Examples 5 to 12 readily establish that at the same ethylenediamine:monoethanolamine molar ratio, the run which also contains ammonia will have a greater selectivity toward the production of noncyclic polyethyleneamines.

Table 2 shows the data with respect to the feed molar ratio of ethylenediamine:monoethanolamine:ammonia in the reactant stream, the selectivity in terms of the percent of noncyclic components in the product mixture, the percent conversion based on the amount of ethylenediamine and monoethanolamine in the reactant feed stream and the yield of noncyclic polyethylene amines. Disregarding Example 6, the non-ammonia containing runs of Examples 9 and 10 in which boron phosphate was used as a catalyst at a 5 mole % level as representative of the prior art gave the highest conversions at about 85% and 66%, respectively. However, the selectivity to noncyclic products was a relatively low 11% and 42%. The ammonia-containing examples all had selectivity values of greater than 50%.

High conversion by itself is not necessarily good. Selectivity data reveals the type of products formed by the consumed reactants. If the conversion of reactants is low, the unconsumed reactants can always be recycled, but if they have been converted to undesirable products, the starting material is lost. Therefore, selectivity and yield values are important data to be considered.

When considering the yield of noncyclic products produced in terms of the amount of ethylenediamine and monoethanolamine consumed, all the ammonia-containing examples were superior, with Examples 8, 11 and 12 which contained boron phosphate as a catalyst demonstrating a very high yield compared to the non-ammonia containing boron phosphate examples.

Examples 2, 4 and 8 demonstrate that predominantly noncyclic polyamines can be obtained by a reaction in which the mole ratio of monoethanolamine:ethylenediamine is greater than 1 if ammonia is included in the reaction mixture.

STATEMENT OF INDUSTRIAL APPLICATION

The inventive process for preparing noncyclic polyalkylene polyamine compounds is applicable to the preparation of linear and branched polyalkylene polyamines which may be used to coagulate or flocculate suspended solids from liquid solutions or slurrys, i.e., accelerate the separation of suspended solids from the suspending liquid phase. Linear and branched polyalkylene polyamines are also used in plasticizers, accelerators and antioxidants for polymers, and as comonomers (with diesters or urea-formaldehyde resins) for production of adhesives, waterproof sealers and protective coatings. In particular, polyethylene polyamines are useful in corrosion inhibitors in coolant and lubricant formulations, preparation of anion exchange resins, finishing agents for textiles and acid gas scrubbing.

We claim:

1. A process for preparing a noncyclic polyalkylene polyamine which comprises:

contacting ammonia, an alkyleneamine compound having two primary amino groups of the general formula:

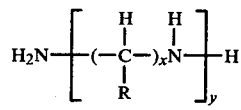

wherein R is hydrogen or a lower alkyl ($C_1$–$C_4$) radical, x is a number from 2 to about 6, and y is a number from 1 to about 4, and an alkanolamine compound having primary or secondary hydroxyl groups of the general formula:

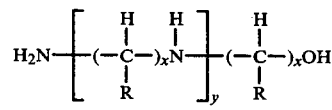

wherein R is hydrogen or a lower alkyl ($C_1$–$C_4$) radical, x is a number from 2 to about 6, and y is a number from 0 to about 3; in the presence of an effective amount of a phosphorus-containing substance or a salt of a sulfur-containing substance, or the corresponding acid, at a temperature sufficient to effect reaction between the ammonia, the alkyleneamine compound and the alkanolamine compound under a pressure sufficient to maintain the reaction mixture essentially in liquid phase.

2. The process of claim 1 wherein the ammonia, alkyleneamine and alkanolamine are contacted in the presence of a phosphorus-containing substance which is selected from the group consisting of acidic metal phosphates, phosphoric acid compounds and their anhydrides, phosphorous acid compounds and their anhydrides, alkyl or aryl phosphate esters, alkyl or aryl phosphite esters, alkyl or aryl substituted phosphorous acids and phosphoric acids, wherein the alkyl groups have from 1 to about 8 carbon atoms and the aryl groups have from about 6 to about 20 carbon atoms, alkaline metal monosalts of phosphoric acid and mixtures of any of the above.

3. The process of claim 2 wherein the phosphorus-containing substance is an acidic metal phosphate.

4. The process of claim 2 wherein the phosphorus-containing substance is boron phosphate.

5. The process of claims 2, 3 or 4 wherein the level of phosphorus-containing substance is from about 0.1 to 25 mole percent based on alkyleneamine and alkanolamine present in the reaction mixture.

6. The process of claim 5 wherein the level of phosphorus-containing substance is from about 0.1 to 10 mole percent.

7. The process of claim 5 wherein the temperature is from about 200° to 350° C.

8. The process of claim 7 wherein the mole ratio of alkyleneamine to alkanolamine is from 5:1 to 1:5.

9. The process of claim 7 wherein the mole ratio of alkyleneamine to alkanolamine to ammonia is from 1-2:1-2:1-10.

10. The process of claim 9 wherein the alkyleneamine is ethylenediamine and the alkanolamine is monoethanolamine.

11. The process of claim 1 wherein the ammonia, alkyleneamine and alkanolamine are contacted in the presence of a salt of a sulfur-containing substance.

12. The process of claim 11 wherein the sulfur-containing substance is an inorganic sulfate.

13. The process of claim 12 wherein the inorganic sulfate is a sulfate of a Group I, II, IIIa, IV, VIb or VIIIb metal.

14. The process of claim 13 wherein the sulfate is beryllium sulfate, boron sulfate or ammonium sulfate.

15. The process of claims 11, 12, 13 or 14 wherein the level of sulfur-containing substance is from about 0.1 to 25 mole percent based on alkyleneamine and alkanolamine present in the reaction mixture.

16. The process of claim 15 wherein the level of the sulfur-containing substance is from about 0.1 to 10 mole percent.

17. The process of claim 15 wherein the temperature is from about 200° to 350° C.

18. The process of claim 17 wherein the mole ratio of alkyleneamine to alkanolamine is from 5:1 to 1:5.

19. The process of claim 17 wherein the ratio of alkyleneamine to alkanolamine to ammonia is from 1-2:1-2:1-10.

20. The process of claim 19 wherein the alkyleneamine is ethylenediamine and the alkanolamine is monoethanolamine.

21. A process for preparing a noncyclic polyethylene polyamine which comprises:
contacting ethylenediamine, monoethanolamine and ammonia in the presence of an effective amount of a phosphorus-containing substance at a temperature from about 200° to 350° C. under at least that pressure which is sufficient to maintain the reaction essentially in liquid phase; and
recovering a noncyclic polyethyelene polyamine.

22. A process for preparing a non-cyclic polyethylene polyamine which comprises:
contacting ethylenediamine, monoethanolamine and ammonia in the presence of an effective amount of a salt of a sulfur-containing substance at a temperature from about 200° to 350° C. under at least that pressure which is sufficient to maintain the reaction essentially in liquid phase; and
recovering a noncyclic polyethylene polyamine.

* * * * *